US006968294B2

United States Patent
Gutta et al.

(10) Patent No.: US 6,968,294 B2
(45) Date of Patent: Nov. 22, 2005

(54) AUTOMATIC SYSTEM FOR MONITORING PERSON REQUIRING CARE AND HIS/HER CARETAKER

(75) Inventors: Srinivas Gutta, Buchanan, NY (US); Eric Cohen-Solal, Ossining, NY (US); Miroslav Trajkovic, Ossining, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 138 days.

(21) Appl. No.: 09/808,848

(22) Filed: Mar. 15, 2001

(65) Prior Publication Data

US 2002/0169583 A1 Nov. 14, 2002

(51) Int. Cl.⁷ .......................... G08B 21/00; G08B 23/00
(52) U.S. Cl. ...................................... 702/188; 600/595
(58) Field of Search ................................. 702/122, 150, 702/188; 704/200, 202; 600/595; 710/18

(56) References Cited

U.S. PATENT DOCUMENTS

| | | | | |
|---|---|---|---|---|
| 3,948,250 A | * | 4/1976 | Weisman ................ 128/2.06 F |
| 4,196,425 A | * | 4/1980 | Williams, Jr. et al. ....... 340/573 |
| 4,524,243 A | | 6/1985 | Shapiro ........................... 179/5 |
| 5,012,522 A | * | 4/1991 | Lambert ......................... 382/2 |
| 5,462,051 A | * | 10/1995 | Oka et al. ..................... 600/300 |
| 5,479,932 A | * | 1/1996 | Higgins et al. .............. 600/529 |
| 5,505,199 A | | 4/1996 | Kim ............................ 128/633 |
| 5,576,972 A | * | 11/1996 | Harrison ..................... 364/516 |
| 5,692,215 A | * | 11/1997 | Kutzik et al. ................ 395/838 |
| 5,905,436 A | | 5/1999 | Dwight et al. ............ 340/573.1 |
| 6,002,994 A | | 12/1999 | Lane et al. .................. 702/188 |
| 6,049,281 A | * | 4/2000 | Osterweil ................. 340/573.4 |
| 6,062,216 A | * | 5/2000 | Corn ...................... 128/204.23 |
| 6,064,910 A | | 5/2000 | Andersson et al. ........... 607/20 |
| 6,160,478 A | * | 12/2000 | Jacobsen et al. ........ 340/539.12 |
| 6,190,313 B1 | * | 2/2001 | Hinkle ........................ 600/300 |
| 6,323,761 B1 | * | 11/2001 | Son ........................ 340/426.35 |
| 6,431,171 B1 | * | 8/2002 | Burton .................. 128/204.18 |
| 6,553,256 B1 | * | 4/2003 | Jorgenson et al. .............. 607/5 |
| 6,796,799 B1 | * | 9/2004 | Yoshiike et al. ............. 434/236 |

FOREIGN PATENT DOCUMENTS

| | | | |
|---|---|---|---|
| DE | 3830655 | 9/1988 | ........... G08B/23/00 |
| EP | 0716402 | 12/1995 | ......... G08B/13/193 |
| GB | 2027312 | 7/1979 | .............. G01S/3/78 |
| GB | 2179186 | 7/1986 | ........... G08B/21/00 |
| WO | WO9725697 | 1/1997 | ........... G08B/21/00 |

OTHER PUBLICATIONS

Patent Abstracts of Japan, Numa Takayuki : "Feeling Analyzing System" Publication No. 2000076421, Mar. 14, 2000, Application No. 10244123, Aug. 28, 1998.

Patent Abstracts of Japan, Samejima Tetsuro: "Monitoring Image Recording And Reproducing Device" Publication No. 09046634, Feb. 14, 1997, Application No. 07190874, Jul. 26, 1995.

* cited by examiner

*Primary Examiner*—Marc S. Hoff
*Assistant Examiner*—Paul Kim
(74) *Attorney, Agent, or Firm*—Gregory L. Thorne

(57) ABSTRACT

A monitoring system for an infant, child, invalid, or other person requiring care uses computer vision and hearing, and inputs of other modalities, to analyze the status of a caretaker and/or cared-for person and its environment. The conditions are classified as normal or alarm conditions and an informative alarm signal is generated which may include records of the vision audio and other inputs. The system also has the ability to solicit responses from the occupants to stimulate a classifiable input to reduce ambiguity in its state signal.

19 Claims, 3 Drawing Sheets

AUTOMATIC SYSTEM FOR MONITORING PERSON REQUIRING CARE AND HIS/HER CARETAKER

BACKGROUND OF THE INVENTION

1. Field of the Invention

The present invention relates to devices that generate an alarm signal when conditions surrounding an invalid, infant, or child, or other person or a caretaker thereof, warrant it.

2. Background

Remote security monitoring systems in which a video camera is trained on a subject or area of concern and observed by a trained observer are known in the art. Also infant or child monitors that transmit audio to a portable receiver are available in the market. These devices, however, require constant attention in order to provide protection to the subject or area of concern, such as an infant or child.

Automated infant or child monitors have been proposed which, for example, monitor an infant's sleeping position to help prevent sudden infant or child death syndrome (SIDS). One approach, suggested in U.S. Pat. No. 5,864,291 uses a breathing-sensing strap around the infant's torso to detect breathing. Another (U.S. Pat. No. 5,638,824) suggests using an ultrasonic sensor and U.S. Pat. No. 5,914,660 position sensors for the same purpose. The automation in these types of monitors, however, provide little use for babies that are distressed for reasons other than a failure to breathe or sleep in an expected position. Also, the alarm signal may contain false positives and is of little help in diagnosing the cause of distress.

A monitored person's physical and emotional state may be determined by a computer for medical diagnostic purposes. For example, U.S. Pat. No. 5,617,855, hereby incorporated by reference as if fully set forth herein, describes a system that classifies characteristics of the face and voice along with electroencephalogram and other diagnostic data to help make diagnoses. The device is aimed at the fields of psychiatry and neurology. This and other such devices, however, are not designed for monitoring persons in their normal environments.

In still another application area, machines automatically detect an occupant's presence or specific features of the occupant for purposes of machine-authorization and authentication or convenience. To that end, some prior art systems employ biometric sensing, proximity detectors, radio frequency identification tags, or other devices.

EP 0716402B1 describes a method of detecting the number of people entering a train or other space using infrared sensors and fuzzy inference techniques. When the number of people is outside desired limits or unbalanced, the system can generate notices to that effect which may be linked to devices to correct the condition.

UK 2027312A describes a method of detecting the movement of fish using IR cameras generating a standard video signal.

U.S. Pat. No. 4,524,243 describes a system in which a user is required to activate a switch at specified intervals. Failure to do so results in the generation of an inactivity alarm.

U.S. Pat. No. 5,905,436 discloses a system in which the failure of various sensors in a home to be triggered results in the generation of a signal at a central monitoring station indicating such. The disclosure is directed at the supervision of an elderly person living at home.

UK 2179186A describes a system in which, if movement not detected at a pre-determined time, an alarm is triggered. A warning is given so that the user can reset the switch.

U.S. Pat. No. 6,002,994 discloses a system in which transmitters, placed at strategic locations in a house, are triggered whenever a person is present at the location of a sensor triggering the transmitter. Also, the system employs other inputs attached to devices and appliances that the user is expected to use. The system is trained to recognize normal patterns of use. The transmitters transmit a signal to a central monitor if the normal pattern is not followed.

In this reference, physiological measurements may include the user's blood pressure, heart rate, body temperature, body weight and blood glucose level. Non-physiological measurements may include room temperature, ammonia from spilled urine, methane from spoiling food, a presence of smoke, frequency of electrical usage, frequency of water usage, temperature of water flowing from a tap, the user's movement within the selected environment as indicated by motion sensors, and use of appliances including a toilet, telephone, stove, microwave oven, toaster, oven, refrigerator, freezer, dishwasher, bath, shower, garbage disposal means, clothes washer, clothes drier, mail box, door and vehicle.

Machine identification of faces is a technology that is well-developed. In GB 2343945A for a system for photographing or recognizing a Face, a controller identifies moving faces in a scene and tracks them to permit image capture sufficient to identify the face or distinctive features thereof. For example, the system could sound an alarm upon recognizing a pulled-down cap or face mask in a jewelry store security system.

There remains a need in the present art for a system that monitors persons requiring supervision to be more robust, capable of responding to more subtle cues and provide more informative information to supervisors.

SUMMARY OF THE INVENTION

Briefly, an alarm system monitors conditions of a person requiring care, others attending to that person, and the environment of that person. The alarm system generates an informative alarm signal or message containing information about the these factors to help the message recipient understand what is going on. In an embodiment, the alarm signal is a live video and/or audio feed from a camera trained on the person requiring care. In another embodiment, the alarm signal is a symbolic set of data relating to the status and the condition that generated the alarm, for example, the message "Person requiring care not attended to in 3 hrs," "No movement detected in 20 min.," "Stopped breathing," or "Caretaker absent." In still other embodiments, the system generates responses to stimulate action, such as a response from a caretaker that is on the premises. The alarm signal may be transmitted by phone line, the Internet, or a wireless channel.

The field of artificial intelligence and robotics has given rise to technology that enables machines to make sufficient sense of their surroundings to recognize predefined conditions, navigate vehicles, and identify objects and their orientations, for example. Components of systems called autonomous observers have been made in the lab which allow a machine to follow an observer in an area and track escape routes. Other applications of similar technology include video tracking systems that follow a speaker giving a presentation and respond to the speaker's gesture commands. In embodiments of the present invention, the technology of image and video recognition, audio recognition, and other inputs may be applied to infer the condition of a monitored person requiring care.

Artificial intelligence (AI) principles are used by a classification engine receiving video, audio, and/or other inputs to model a current situation. When conditions are classified as calling for attention (distress event), video, audio, and other data that may be buffered up to the distress event, as well as live data, may be transmitted to a monitor along with an indication of the class to which the recognized event belongs. For example, the audio signal generated by a crying person requiring care may be classified as a "person-crying" condition either alone or in concert with the classification of other data such as video data of the crying person requiring care. Condition classes for a suitable monitor system may include events such as:

1. trigger by a breathing sensor, motion sensor, or audio sensor as in prior art devices,
2. delay in response time of a nanny or au pair or other care-giver given to a person requiring care,
3. movement (crawling) of the person requiring care into prohibited areas of a room,
4. sudden movement consistent with falling, running, normal walking, crawling, etc.,
5. lack of normal movement such as rapid movement such as an infant or child being picked up at a time other than a previously defined time,
6. presence of the person requiring care or other individuals in a space and their number,
7. consistency of the clothing, facial features, etc. of the occupants of a space throughout a period of time.
8. loud sounds, normal sounds, and unusual sounds, based upon signature of sound,
9. location of sound source,
10. occupancy of unauthorized spaces,
11. occupancy patterns, for example whether care-giver is spending unusual amounts of time away from person requiring care or care-giver is spending unusual amounts of time in a particular space,
12. patterns consistent with damage to the monitoring system,
13. voice signatures of unauthorized occupants or unrecognized voice signatures,
14. body habitus and physiognomy of occupants,
15. status of security system in the space,
16. unrecognized objects in occupied spaces or recognized objects being moved or found in unexpected locations,
17. temperature, humidity, sound levels, or other ambient variables out of normal range,
18. failure to detect face of a care-giver over crib for a specified interval,
19. presence of an unrecognized face or body pattern, The event that triggers an alarm condition may be a simple one such as prior art sensors that monitor breathing or crying, or they may be more complex ones that integrate multiple inputs into a network to make decisions as to the alarm status. Such network devices may include classifiers in the form of neural networks, Bayesian networks, and other techniques for machine-recognition of physical objects and behaviors. The art in this field is rich and rapidly-growing and it is expected that improved means for implementing the current invention will continually become available. Preferably the classification engine is trainable so that it does not need to rely solely on predefined template patterns for pattern-matching. The system may be provided with the ability to generate a simulated dialogue to provide for assistance in training such as asking an occupant to select from among a number of condition classes present in a monitored space at a time when the occupant can observe the monitored space.

In an embodiment, the present invention may also employ simulated dialogue with a machine-generated persona such as disclosed in the following references, each of which is incorporated in its entirety as if fully set forth herein.

U.S. Pat. Ser. No. 09/699,606 for Environment-Responsive User interface/Entertainment Device That Simulates Personal Interaction;

U.S. Pat. Ser. No. 09/686,831 for Virtual Creature Displayed on a Television; and U.S. Pat. Ser. No. 09/699,577 for User interface/Entertainment Device That Simulates Personal Interaction and Responds to Occupant's Mental State and/or Personality.

The persona may, in response to a particular condition (ambiguous classification of extant conditions or just on a random or interval time basis) request information from occupants about present circumstances. The feedback received may be used by the classification engine to further infer the extant conditions and/or relayed to a responsible party along with other information about circumstances.

The above applications also discuss the topic of classifying a rich array of inputs to make decisions about occupants.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE PREFERRED EMBODIMENTS

Figure 1:
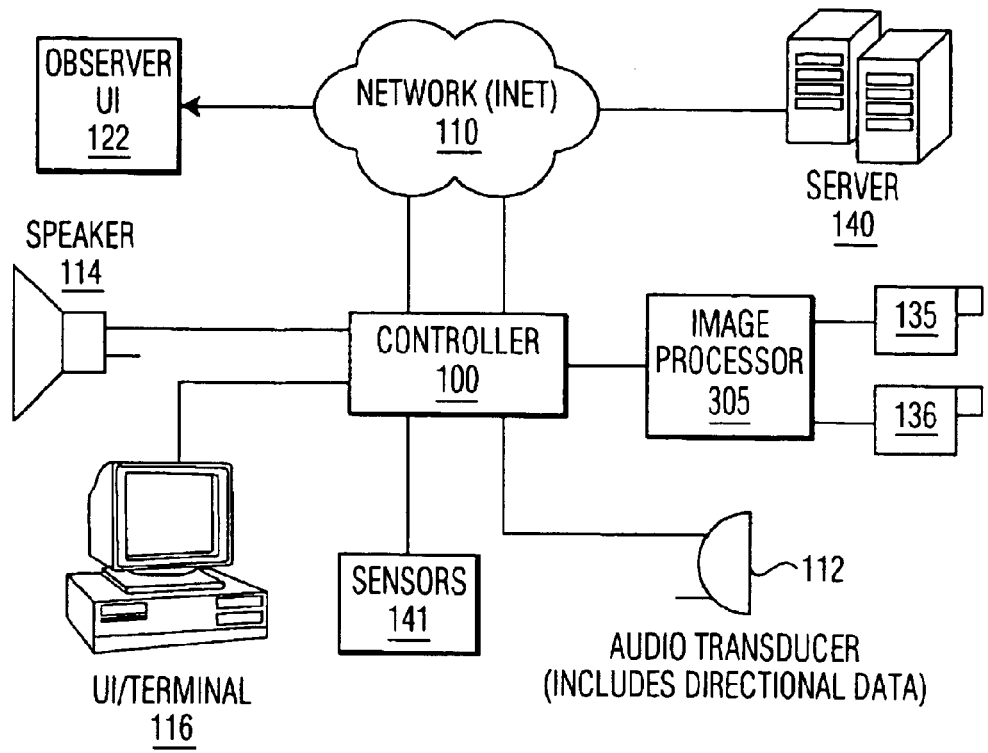
FIG. 1 is a schematic representation of a hardware system capable of supporting a monitor system according to an embodiment of the invention.

Referring to FIG. 1, in a hardware apparatus for implementing an embodiment of the invention, a programmable controller 100 receives input from various sources, for example, a connected image processor 305 connected to cameras 135 and 136, microphone 112, and sensors 141.

Sensors 141 may include alarm sensors such as breathing monitors or other SIDS prevention detectors or any other type of sensor such as temperature sensors, position sensors, security switches, proximity sensors, electrical load sensors, ambient light sensors, etc. Data for updating the controller's 100 software or providing other required data, such as templates for modeling its environment, may be gathered through local or wide area or Internet networks symbolized by the cloud at 110. An Observer UI 122 and Server 140 are coupled to the network cloud 110. The controller may output audio signals (e.g., synthetic speech or speech from a remote speaker) through a speaker 114 or a device of any other modality. For programming and requesting occupant input, a terminal 116 may be provided.

Figure 2:
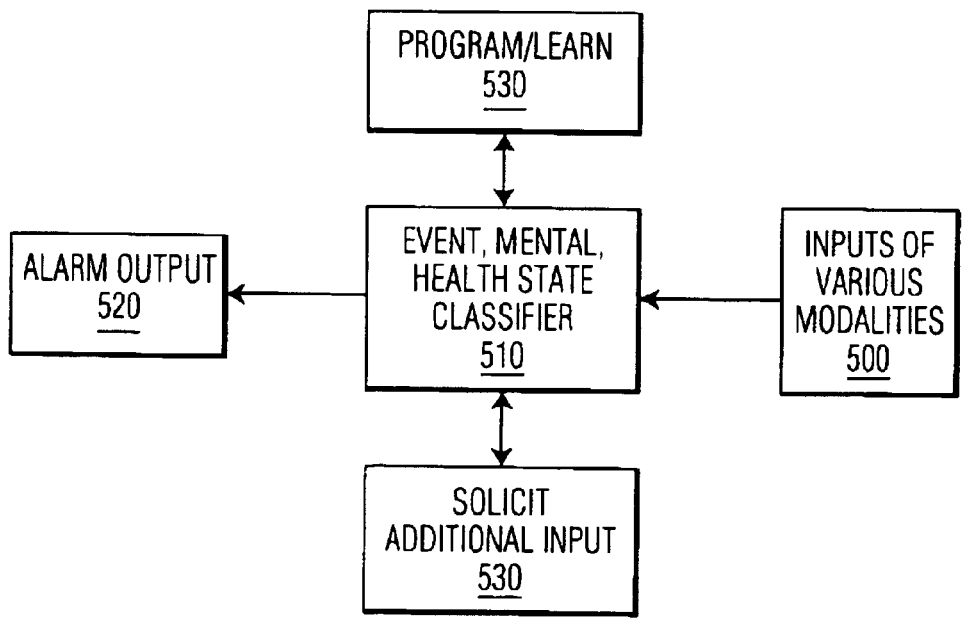
FIG. 2 is a high level flow diagram illustrating how inputs of various modalities may be filtered to generate an alarm signal consistent with several embodiments of the invention.

FIG. 2 illustrates how information gathered by the controller 100 of FIG. 1 may be used to identify particular conditions and generate an alarm responsive to those conditions. Inputs of various modalities 500 such as video data, audio data, environmental conditions such as temperature, sound level, security system status, etc. are applied to a trained classifier 510 to discriminate and classify distinguishable features of a monitored environment. For example, the classifier 510 may be trained to discriminate faces and to classify them as belonging to one of a recognized set or not belonging to any member of the recognized set. For another example, the classifier 510 may be trained to classify sudden noises like breaking glass or falling objects. Still other examples are training it to recognize the emotional status and health of the monitored person by facial expression, physiognomy, body habitus, behavior, etc. from data in a video signal. Each classification of events/status may then be combined and further classified as an alarm condition. For example, the classifier may be trained to identify a loud sound followed by an unrecognized face as an alarm condition.

The technologies for training such classifiers as 510 are well developed and growing fast. Such classifiers may be trained explicitly using rules to form, for example, a Bayesian classifier. Alternatively, they may be trained using examples, as for training a neural net. Since the subject of how different kinds of classifiers are designed and trained is not the focus of the present invention, except as discussed herein, and because the technology for designing and training such classifiers is well-developed and highly varied, the particulars are not discussed in detail presently. Some interface for programming and/or training the classifier 510 is indicated 530. The end goal of the classifier 510 is to output status or alarm information to an alarm output 520. Both 530 and 520 may be networked terminals, cell phone devices, PDAs, or any suitable UI device.

Figure 3:
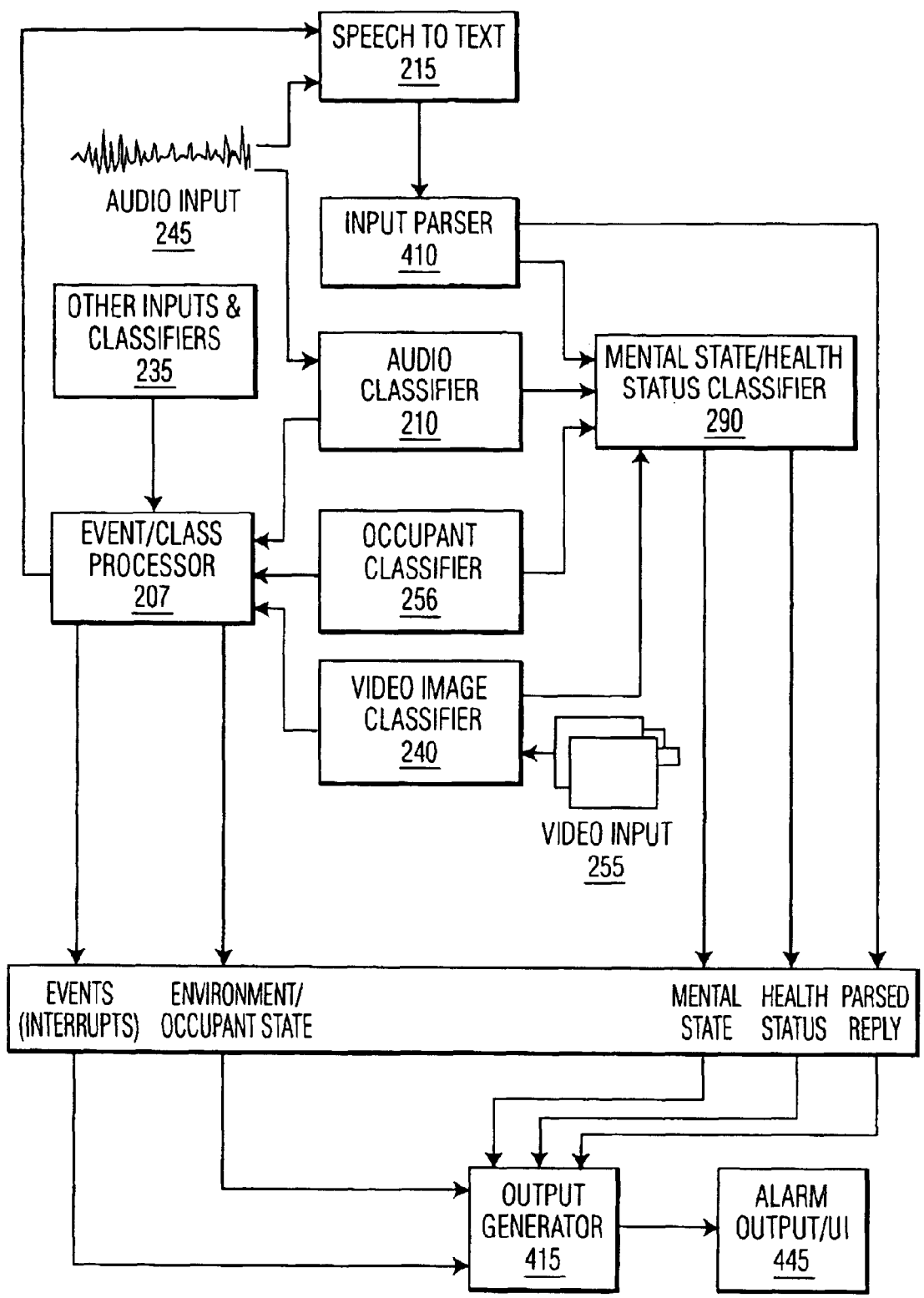
FIG. 3 is a functional diagram of a software system for implementing a monitor system according to an embodiment of the invention.

Referring now to FIG. 3, a functional diagram of an event driven architecture that may be used to monitor an occupied zone separates the object illustrated by the single "black box" of classifier 510, into multiple objects whose outputs are combined to classify alarm conditions. Audio input 245, video input 255, and other user interface devices (not shown) generate signals that are applied to respective classifiers 210, 240. The audio input 245, which may be received by a microphone (not shown separately) or a directional audio detector (not shown separately) which indicates both the sound and its direction, or any other suitable audio transducer, may be applied to an audio classifier 210. The latter data form a real-time signal, which the audio classifier 210 classifies by suitable digital or analog means or a combination thereof. The audio classifier 210 then generates a current state information signal which it applies to both a mental state/health status classifier 290 and an event/class processor 207.

To illustrate, the signal generated by the audio classifier may be a vector that includes the following components.

1. Identity of speaker,
2. Number of speakers,
3. Type of sound (crashing, bumping, periodic, tapping, etc.)
4. Sound intensity level,
5. Duration, time of day, of distinguished sound,
6. Quality of speech (whispering, yelling, rapid, etc.)
7. Quality of voice (masculine, feminine, child, etc.),
8. Identified event (switching of a light, snoring, tinny sound of a radio or TV, vacuum cleaner, etc.)

Each instance of a discrete sound event and/or state may be combined with a time stamp indicating the time it began and, if it has, ended, and the combined vector signal applied to the event/class processor 207.

A video image classifier 240 receives video input 255, classifies image data and generates state information signals which are applied to the mental state/health status classifier 290 and the event/class processor 207. The video image classifier 240 may be programmed to identify certain events such as gestures, rapid movement, number of occupants in its field of view, etc. Like the audio classifier 210, its output may be a vector which, for illustrative purposes, includes the following components.

1. Number of occupants,
2. Identity of occupants (including unrecognized) which may derive information from body, facial features, movement, etc.,
3. Body position/gesture of each occupant (e.g., standing, seated, drinking, eating,
4. Sizes of transient objects in scene,
5. Nature of transient objects in scene (e.g., television, dinner plate, laundry basket, etc.),
6. Rapidity of movement of image center of occupants as an indication of running or chaos,
7. Change in camera angle, etc.

Video processing techniques from various fields such as authentication, gesture control of machines, etc. may be employed in the current system according to the particular aims of the system designer.

Other input devices with associated classifiers 235 apply their output signals to the event/class processor 207. The other UI classifiers 235 may include instrumentation monitoring the environment such as ambient light level, time of day, temperature of the room, security status of a building, etc.

Text data may be obtained from a speech to text converter 215 which receives the audio input 245 and converts it to text. When obtained from audio, the text may be time-stamped by the speech to text converter 215. The speech to text converter 215 parses the text using grammatical or structural rules such as used in new or prior art conversation simulators, as used in natural language search engines, or other suitable means. The result of this parsing is the extraction of words or utterance features that the mental state/health status classifier 290 may recognize. Parsing may be done using rule-based template matching as in conversation simulators or using more sophisticated natural language methods. Words indicative of mood may then be sent to the mental state/health status classifier 290 for classification of the mood of the speaker.

The mental state/health status classifier 290 receives signals from the various classifiers and processes these to generate a mood/personality state signal. The mental state/health status classifier 290 may be a trained neural network, a Bayesian network, a simple rule-based system, or any other type of classifier capable of taking many different inputs and predicting a probability of the occupant being in a given emotional state and having a given personality. Various personality and mood typologies may be used, running from simple to complex. An example of set of rules for classifying an occupant as bored is:

- low sentence/phrase word count (the occupant's sentences contain few words) (input parser 410 signal indicating response word count),
- a low incidence of words suggesting enthusiasm such as superlatives (input parser 410 signal indicating adjectives),
- a quiet flat tone in the voice (audio classifier 210 signal indicating modulation inflection intensity),
- a lack of physical movement (video image classifier 240 signal indicating , etc.,
- little movement of the head or body,
- sighing sounds, etc.
- looking at watch.
- lack of eye contact with objects such as television or book in the scene.

Each of these may be classified by the corresponding classifier. The color of the occupant's clothes, the pitch of the occupant's voice, the number of times the occupant enters and leaves a single scene, the way the occupant gestures, etc. all may provide clues to the occupant's emotional state and/or personality. The output vector may be any suitable mental state classification. For example, the valence/intensity emotional state typology suggested in U.S. Pat. No. 5,987,415 may be used.

The following tables summarize the Big Five which is an evolutionary outgrowth of the Myers-Briggs typology. There are many academic papers on the subject of modeling emotional states and personalities and many of these address the issues of machine classification based on voice, facial expression, body posture, and many other machine-inputs. Even the weather, which may be obtained using an agent over the Internet or via instruments measuring basic weather data such as daily sunshine, may be used to infer mental emotional state.

The Six Facets of Negative Emotionality (adapted from Costa & McCrae, 1992) with Anchors for the Two Extremes of the Continuum

| Six Facets of Negative Emotionality | RESILIENT R+− | REACTIVE R− |
|---|---|---|
| Worry | Relaxed; calm | Worrying; uneasy |
| Anger | Composed; slow to anger | Quick to feel anger |
| Discouragement | Slowly discouraged | Easily discouraged |
| Self-Consciousness | Hard to embarrass | More easily embarrassed |
| Impulsiveness | Resists urges easily | Easily tempted |
| Vulnerability | Handles stress easily | Difficulty coping |

The Six Facets of Extraversion (adapted from Costa & McCrae, 1992) with Anchors for the Two Extremes of the Continuum

| Six Facets of Extraversion | INTROVERT E− | EXTRAVERT E+ |
|---|---|---|
| Warmth | Reserved; formal | Affectionate; friendly, intimate |
| Gregariousness | Seldom seeks company | Gregarious, prefers company |
| Assertiveness | Stays in background | Assertive; speaks up; leads |
| Activity | Leisurely pace | Vigorous pace |
| Excitement-Seeking | Low need for thrills | Craves excitement |
| Positive Emotions | Less exuberant | Cheerful; optimistic |

The Six Facets of Openness (adapted from Costa & McCrae, 1992) with Anchors for the Two Extremes of the Continuum

| Six Facets of Openness | PRESERVER O− − | EXPLORER O+ |
|---|---|---|
| Fantasy | Focuses on here and now | Imaginative; daydreams |
| Aesthetics | Uninterested in art | Appreciates art and beauty |
| Feelings | Ignores and discounts feelings | Values all emotions |
| Actions | Prefers the familiar | Prefers variety; tries new things |
| Ideas | Narrower intellectual focus | Broad intellectual curiosity |
| Values | Dogmatic; conservative | Open to reexamining values |

The Six Facets of Agreeableness (adapted from Costa & McCrae, 1992) with Anchors for the Two Extremes of the Continuum

| Six Facets of Agreeableness | CHALLENGER A− | ADAPTER A+ |
|---|---|---|
| Trust | Cynical; skeptical | See others as honest & well-intentioned |
| Straightforwardness | Guarded; stretches truth | Straightforward, frank |
| Altruism | Reluctant to get involved | Willing to help others |
| Compliance | Aggressive; competitive | Yields under conflict; defers |
| Modesty | Feels superior to others | Self-effacing; humble |
| Tender-Mindedness | Hardheaded; rational | Tender-minded; easily moved |

The Six Facets of Conscientiousness (adapted from Costa & McCrae, 1992) with Anchors for the Two Extremes of the Continuum

| Six Facets of Conscientiousness | FLEXIBLE C− | FOCUSED C+ |
|---|---|---|
| Competence | Often feels unprepared | Feels capable and effective |
| Order | Unorganized; unmethodical | Well-organized; neat; tidy |
| Dutifulness | Casual about obligations | Governed by conscience; reliable |

-continued

| Six Facets of Conscientiousness | FLEXIBLE C− | FOCUSED C+ |
|---|---|---|
| Achievement Striving | Low need for achievement | Driven to achieve success |
| Self-Discipline | Procrastinates; distracted | Focused on completing tasks |
| Deliberation | Spontaneous; hasty | Thinks carefully before acting |

The mental state/health status classifier 290 outputs a state vector, with a number of degrees of freedom, that corresponds to the models of personality and mental state chosen by the designer. The mental state/health status classifier 290 may cumulate instantaneous data over a period of time in modeling personality, since this is a persistent state. The mental state will have more volatile elements.

The event/class processor 207 is a classifier that combines state information from multiple classifiers to generate an environment/occupant state signal indicating the current status of the system's environment, including the occupants, particularly the monitored person. The event/class processor may also generate event signals (interrupt signals) to ensure an instant response when certain events are recognized by the classifiers, for example, events that may coincide with an emergency condition. The recognition of events may require state information from multiple classifiers, so the event/class processor 207 combines state data from multiple classifiers to generate a combined state signal and a combined event signal. The environment/state signal may include an indication of all the possible event classes the various classifiers are capable of identifying or only those surpassing a threshold level of confidence.

The output generator 415 receives the mood/personality state vector and parsed reply data from the mental state/health status classifier 290 and input parser 410 respectively. The response generator 415 also receives the environment/occupant state signal and events signal from the event/class processor 207. The output generator 415 selects a type of response corresponding to the mental state, the environment/occupant state, and the events signal from an internal database and generates an alarm output if required. Alternatively, the output generator may be programmed to select an output template that solicits further data from an occupant through user interface, such as the terminal 116 (FIG. 1). For example, if the various classifier output components indicate low confidence levels, the system could generate speech through the speaker 114 asking for information about the current state of the occupied space. For example "Is anyone there" could be generated if no clear presence of an adult can be detected. The system then uses its other input devices, such as video input 255, to decrease ambiguity in its status and event signals. Note that these features may be implemented through a conversation simulator as described in U.S. patent Ser. Nos. 09/699,606, 09/686,831, and 09/699,577 may be built into the system to operate as a machine assistant.

Tracing the data flow beginning with the video input 255, the video input 255 signal is applied to the video image classifier 240. The video image classifier 240 is programmed to recognize a variety of different image and video-sequence classes in the video input 255 signal. For example, it may be programmed to distinguish between a person sitting up and lying down; between a person sitting still and one moving agitatedly or leaving an area; etc. A probability for each of these classes may be generated and output as a signal. Alternatively, a single, most-probable class may be generated and output as a signal. This signal is applied to the event/class processor 207, which combines this data with other class data to generate an environment/occupant state signal. If the event/class processor 207 receives an indication from the video image classifier 240 that something sudden and important has occurred, for example, the occupant has gotten up and left the room, the event/class processor 207 will generate an event signal. If the mental state/health status classifier 290 receives a signal from the video image classifier 240, indicating the occupant is moving in a fashion consistent with being agitated, that mental state/health status classifier 290 may combine this information with other classifier signals to generate a mood/personality state vector indicating an emotional state of heightened anxiety. For example, the audio classifier 210 may be contemporaneously indicating that the speaker's voice is more highly pitched than usual and the input parser 410 may indicate that the word count of the most recent utterances is low.

Note that to allow the system to determine whether a current class or state represents a change from a previous time, the event/class processor 207 and the mental state/health status classifier 290 may be provided with a data storage capability and means for determining the current occupant so that corresponding histories can be stored for different occupants. Identification of occupants, as mentioned above, may be by face-recognition by means of the video image classifier 240, voice signature. It may also be confirmed by radio frequency identification (RFID) token, smart card, or a simple user interface that permits the occupant to identify him/herself with a biometric indicator such as a thumbprint or simply a PIN code. In this way, both the mental state/health status classifier 290 and event/class processor 207 may each correlate historical data with particular occupants and employ it in identifying and signaling trends to the output generator 415.

The event/class processor 207 receives class information from the audio classifier 210 and other classifiers and attempts to identify these with a metaclass it is trained to recognize. That is, it combines classes of states to define an overarching state that is consistent with that multiple of states. Of course, the architecture described herein is not the only way to implement the various features of the invention and the event/class processor 207 could simply be omitted and its functions taken over by the output generator 415. One advantage of separating the functions, however, is that the event/class processor 207 may employ a different type of classifier than the one used by the output generator 415. For example, the output generator 415 could use a rule-based template matcher while the event/class processor 207 could use a trained neural network-type classifier. These allocations of functions may be more suitable since the number of outputs of the output generator 415 may be much higher than the number of classes the event/class processor 207 (or the other classifiers) is trained to recognize. This follows from the fact that network-type classifiers (such as neural network and Bayesian network classifiers) are difficult to train when they have a large number of possible output states.

The video image classifier 240 process may contain the ability to control the cameras (represented by video input 255) that receive video information. The video image classifier 240 may contain a process that regularly attempts to distinguish objects in the room that may or may not be individuals and zoom on various features of those individuals. For example, every time a video image classifier identifies a new individual that image classifier may attempt to identify where the face is in the visual field and regularly zoom in on the face of each individual that has been identified in the field of view in order to obtain facial expression information which can be used for identifying the individual or for identifying the mood of the individual.

We note that the invention may be designed without the use of artificial intelligence (AI) technology as described above, although of robustness of AI technology makes it highly desirable to do so. For example, an audio signal may be filtered by a bandpass filter set for detection of loud crashing sounds and a detector that sets a time-latch output when the filter output is above certain level. Concurrently, a video luminance signal may be low pass filtered and when its energy goes beyond a certain level, it also sets a time-latch. If both latched signals go positive (loud sound and great activity in temporal proximity), the system may generate an alarm.

Alarm signals may include simply some kind of notification of an alarm status. Preferably, however, alarms should be informative as possible within the specified design criteria. For example, an alarm signal may contain audio and/or video data preceding and following the event(s) that triggered the alarm status. These could be recorded by the output generator 415 and transmitted by email, streamed through a cell-phone connection or wireless convergence device with video capability, or some other means. Symbolic representations of the most significant state classes that gave rise to the meta-classification of the alarm condition may also be transmitted. For example, a symbol indicating "loud noise" and/or unrecognized occupant may be transmitted to, say, a text pager used by a responsible party.

Figure 4:
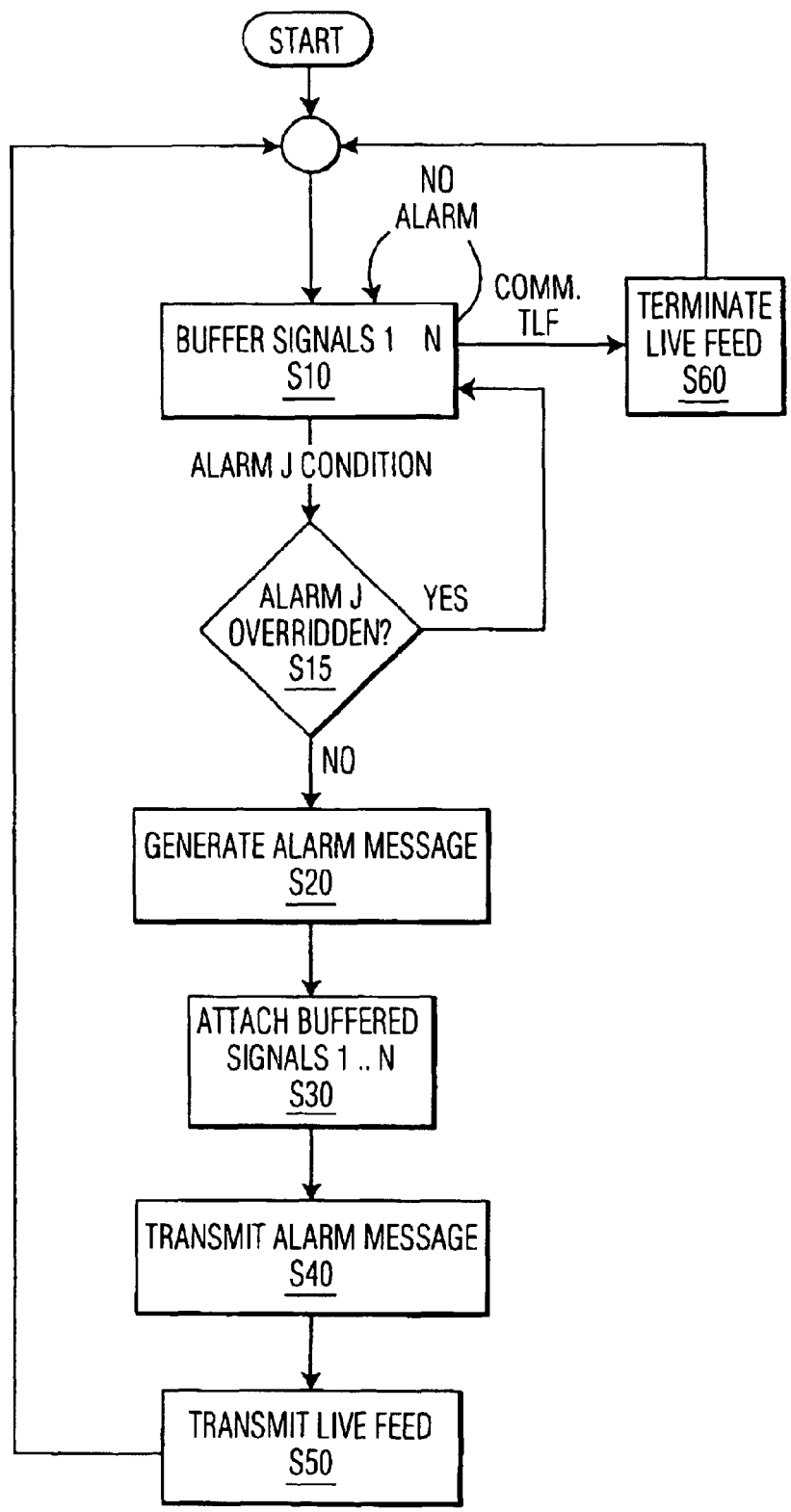
FIG. 4 is a flow chart illustrating the generation of an alarm signal according to an embodiment of the invention.

Referring now to FIG. 4, an arbitrary number of signals may be buffered continuously as illustrated by step S10. If an alarm condition is indicated, at step S15 it is determined if the particular alarm condition had been previously overridden. If it had, buffering of signals is resumed and no further action is taken. If the alarm condition had not been overridden, a message is generated at step S20 and the buffered signals 1 . . . N attached at step S30. The alarm message is then transmitted, for example by email, in step S40 and an optional live feed generated at step S50 if appropriate. The live feed may be made available at a URL included in an email transmission or as a portion of a signal in a message transmitted by an automated telephone call to a digital video telephone.

The buffered signal may be no more than a time sequence indicating the status of one or more sensors over time. The buffered signals need not be signals that caused the indication of an alarm condition. For example, in an embodiment of the invention, a video camera may be trained on a person's bed. The alarm may be generated by a mechanical sensor (such as a chest strap) that detects breathing. The video signal buffer up till the moment of the detection of the person's cessation of breathing may be the signal that is transmitted as part of the alarm message. The length of the buffer may be as desired.

Each alarm may be a unique event, but each may also be generated by the same persistent condition, for example a failure of an infant or child to breathe for a period of time. It is desirable for a given alarm to be acknowledged so that a new alarm condition, arising from different circumstances, is not confused as the existing alarm currently being attended to. One way to handle this is to assign a signature to each alarm based on a vector of the components that gave rise to the alarm condition. The recognition of the same alarm condition would give rise to another vector which may be compared to a table of existing alarms (at step S15) to see if the new alarm had already been overriden. The components may be quantized to insure against small differences in vector components being identified as different or a low sensitivity comparison may be used to achieve the same effect.

Alarm signals may be transmitted by any of the following means.

1. Automatic telephone call with synthetic voice providing symbolic indication of alarm condition (pre-recorded phrases or synthetic speech) and/or buffered audio and/or live audio fed from the monitored space.
2. Wireless appliance with video may include the above plus recorded and/or live data plus text messages providing same information.
3. E-mail message, may contain links to a URL with live or recorded data or may have embedded MIME attachment providing still or moving images.
4. Broadcast: radio message, audio message, display on a wired console, etc.

The following are several example applications and use scenarios.

EXAMPLE 1

An infant's crib is placed against a wall with one or more cameras 135, 136 aimed at a side of the crib where a caretaker would ordinarily stand to view the infant. A microphone 112 is placed in a position to pick up sounds near the crib. The controller 100 receives live video and audio signals from the camera and microphone and filters them through respective classifiers 240 and 210, respectively. The controller 100 is programmed to recognize the caretaker's face and produces a signal indicating that a face is present and a reliability estimate indicating how well the face matches expectation. The controller 100 may be programmed to recognize other faces as well, such as relatives of the baby and children. The controller 100 is further programmed to recognize the sound of crying and produce a signal indicating that crying is present. In addition, the controller 100 is programmed to recognize the following events and produce corresponding signals: normal and abnormal body habitus of the infant, facial expression of infant indicating mood such as crying, content, playing, distressed, moving quickly or slowly, the number of individuals present, presence of new objects in the room and their "blob" sizes ("blob" is a term of art characterizing any closed connected shape that an image processor can define in a video image), mood of recognized face of caretaker.

In the above example, the following events may occur. The infant cries and the caretaker fails to respond. The infant's mood is detected by the audio and video signals received. A synthetic voice calls to the caretaker via the speaker 114 requesting assistance for the infant. The elapsed time from the recognition of the infant's distress till the present reaches a specified interval triggering an alarm. The alarm signal includes a text message, buffered video and buffered audio from a time prior to the alarm event. The alarm signal is sent by email.

EXAMPLE 2

The system configuration of example 1 is included in the present example. Additional cameras and microphones are located at various locations in a house. The baby's presence on a couch is detected. The caretaker is recognized on the couch. The sound of the television is detected. The body position of the adult caretaker is detected in a sleeping position. The system generates synthetic speech requesting for the caretaker to wake up and attend the infant (the programming of the controller 100 being a reflection of a concern that the infant is not in a safe place to be unattended. After a predefined interval during which continued sleep (or illness or death) is detected, an alarm is generated. The alarm contains still images from the video (from a time prior to the alarm) of the sleeping adult and infant and live audio and video of the room in which the infant and adult are located.

EXAMPLE 3

The physical configuration (including programming) of Example 2 is incorporated in the present example. In this example, the infant and crib are replaced by a sick adult and the caretaker is an adult. The supervisor is an agency that supplied the nurse. The alarm condition detected by the system is the lack of movement of any articles or persons in the house. The recognition of occupants, facial recognition, body habitus and body positions, audio, etc. are producing indications of a presence of an adult in a living room, but the signals are low reliability and there is no indication of activity (movement of the occupant). The system is programmed to generate an alarm if none of a set of expected events such as appearance of a recognized face at the bedside of the sick person, movement plus a recognized body position of a person in expected locations in a house, etc. for a predefined interval. The alarm signal contains a live video and audio feed which is controllable by the supervisor (who can switch views, etc. and communicate with the caretaker).

EXAMPLE 4

The system of Example 3 is incorporated in the present example. A babysitter is taking care of multiple children. The system is programmed to recognize the babysitter's face and the faces of the children along with various characterizing features of these people such as body shape, movement patterns, etc. The system is programmed to generate an alarm, and transmit it to a wireless handheld device, when either of the following occurs: (1) the number of occupants detected in the house (the system detects simultaneously at multiple cameras, a particular number of individuals) is greater than a predefined number (presumably the babysitter plus the children) or (2) the system detects an unrecognized face (i.e., it receives a good image of a face, but cannot produce a reliable match with a known template), (3) doors left open for extended periods of time (as indicated by security system status), (4) movement of persons in the house is excessive potentially indicating roughhousing or abuse.

Although in the embodiments described, the visage, location, and activities of both caretaker and person requiring care were monitored, it is possible to monitor only one or the other rather than both. Also, the notion of "occupants" recognized or not, may be applied as well to pets as to human occupants, although admittedly, the state of the art may not be at a point where pet's facial features may be distinguished from those of other animals, certainly the blob-recognition is at a point where it can distinguish between a poodle and cat or other kinds of animals and/or animate objects such as robots.

While the present invention has been explained in the context of the preferred embodiments described above, it is to be understood that various changes may be made to those embodiments, and various equivalents may be substituted, without departing from the spirit or scope of the invention, as will be apparent to persons skilled in the relevant art.

What is claimed is:
1. A monitoring device, comprising:
a controller programmed to receive at least one monitor signal from an environment monitor located in a monitored zone in which a person requiring supervision is located, wherein said at least one monitor signal includes at least one of video and audio data;
said controller being programmed to produce class data by classifying at least one alarm condition in the monitored zone in a class selected from a plurality of available classes, responsive to said at least one monitor signal;
wherein the at least one alarm condition indicates that an event that is threatening to the person has occurred; and
said controller being programmed to generate an alarm signal responsively to said class data and to initiate a transmission of the alarm signal to a remote supervisor, said alarm signal including at least a portion of said at least one monitor signal at least one of immediately prior to and immediately after an incidence of said at least one alarm condition, wherein said controller is programmed to recognize faces and said at least one alarm condition is responsive to at least one of: (a) a failure to detect a face of the person in the monitored zone, and (b) a presence of an unrecognized face in the monitored zone.

2. A monitoring device as in claim 1, wherein said controller is programmed to solicit an action by an occupant, said at least one monitor signal being responsive to said action by said occupant.

3. A monitoring device as in claim 1, wherein said at least one monitor signal includes a signal from a detector configured to detect a lapse in breathing by said person.

4. A monitoring device as in claim 1, wherein said alarm signal includes at least a portion of said at least one monitor signal immediately prior to and immediately after an incidence of the at least one alarm condition.

5. A monitoring device as in claim 1 wherein said alarm signal includes at least one of an audio signal, text data signal, and a video signal.

6. A monitoring device as in claim 1, wherein:
the transmission comprises an indication of the class to which the at least one alarm condition belongs.

7. A monitoring device as in claim 1, further comprising:
buffering the at least one monitor signal to provide the at least a portion of the at least one monitor signal in the alarm signal.

8. A monitoring device comprising:
a controller programmed to receive at least one monitor signal from an environment monitor located in a monitored zone in which a person requiring supervision is located, wherein said at least one monitor signal includes at least one of video and audio data;
said controller being programmed to produce class data by classifying at least one alarm condition in the monitored zone in a class selected from a plurality of available classes, responsive to said at least one monitor signal;
wherein the at least one alarm condition indicates that an event that is threatening to the person has occurred; and
said controller being programmed to generate an alarm signal responsively to said class data and to initiate a transmission of the alarm signal to a remote supervisor, said alarm signal including at least a portion of said at least one monitor signal at least one of immediately prior to and immediately after an incidence of said at least one alarm condition, wherein said controller is programmed to recognize a speaker's voice, and said alarm signal is responsive to at least one of: (a) a failure to recognize a voice of the person, and (b) a presence of a voice of an unrecognized or unauthorized person.

9. A monitoring system, comprising:

a controller connected to receive at least one signal from at least one sensor for monitoring an environment of a person requiring supervision; said at least one sensor generating first and second signals responsive to a state of a caretaker of said person and a state of said person, respectively;

said controller being programmed to determine whether to generate a first alarm signal based on whether the state of the caretaker represents a distress event for the person, and to determine whether to generate a second alarm signal based on the state of the person.

10. A monitoring system as in claim 9, wherein said first alarm signal includes a sample of at least one of said first and second signals.

11. A monitoring system as in claim 9, wherein said controller is programmed to generate a message to solicit an action by said caretaker when said first alarm signal is generated.

12. A monitoring system as in claim 9, wherein:

the at least one sensor is positioned according to an expected location of the caretaker relative to the person.

13. A monitoring system as in claim 9, wherein:

said controller generates the first alarm signal when the state of the caretaker is outside a first specified range; and said controller generates the second alarm signal when the state of the person is outside a second specified range.

14. A monitoring method, comprising the steps of:

monitoring a person requiring supervision by generating a first signal indicative of a status of at least one of the person and an environment of the person; detecting when a behavior of a second person in the environment, other than said person requiring supervision, represents a distress event for the person requiring supervision so as to require the attention of a remote supervisor; and transmitting a signal including at least one of audio, video, and text data to said remote supervisor when the step of detecting detects that the behavior of the second person requires the attention of the remote supervisor.

15. A monitoring method as in claim 14, wherein said person requiring supervision is an infant and said step of detecting includes detecting a lapse of breathing of said infant.

16. A monitoring method as in claim 14, wherein said step of detecting includes detecting at least one of an audio signal and video signal and classifying a predefined pattern in said at least one of an audio signal and a video signal.

17. A monitoring method as in claim 14, wherein:

said step of detecting includes at least one of recognizing a face of said person requiring supervision or the second person, classifying a body habitus of said person requiring supervision, classifying a physiognomy of said person requiring supervision, detecting a speed of movement of said person requiring supervision or said second person, detecting a number of persons in an occupied zone in the environment, and recognizing a voice signature; and said steps of recognizing, classifying, and detecting are automatic machine processes.

18. A monitoring method as in claim 14, wherein said step of detecting includes detecting at least one of a movement or lack thereof and a speech or lack thereof, of at least one of said person and said second person.

19. A monitoring method as in claim 14, wherein:

the signal transmitted to the remote supervisor includes at least a portion of said first signal.

\* \* \* \* \*